United States Patent [19]

Ritter et al.

[11] Patent Number: 4,532,259
[45] Date of Patent: Jul. 30, 1985

[54] BIS[(FLUORO- AND CHLORO-METHYLTHIO)FORMAMIDES], A PROCESS FOR THEIR PREPARATION AND THEIR USE

[75] Inventors: Helmut Ritter, Wuppertal; Wilfried Paulus; Hermann Genth, both of Krefeld, all of Fed. Rep. of Germany

[73] Assignee: Bayer Aktiengesellschaft, Leverkusen, Fed. Rep. of Germany

[21] Appl. No.: 448,588

[22] Filed: Dec. 10, 1982

[30] Foreign Application Priority Data

Dec. 24, 1981 [DE] Fed. Rep. of Germany ....... 3151445

[51] Int. Cl.³ .................... A01N 37/18; C07C 83/10
[52] U.S. Cl. ........................... 514/608; 260/453 RW
[58] Field of Search ................. 260/453 RW; 424/324

[56] References Cited

FOREIGN PATENT DOCUMENTS 0008731 8/1979 Fed. Rep. of Germany ...... 260/453 RW

Primary Examiner—Henry R. Jiles
Assistant Examiner—Robert C. Whittenbaugh
Attorney, Agent, or Firm—Sprung, Horn, Kramer & Woods

[57] ABSTRACT

The new bis[(fluoro- and chloro-methylthio)formamides] of the formula

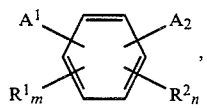

in which $A^1$ and $A^2$ are identical or different and represent the radical

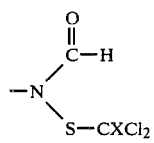

or the radical

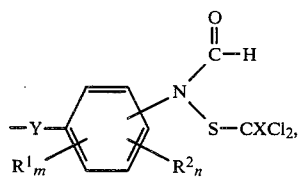

wherein $R^1$ denotes an optionally halogenated lower alkyl or alkoxy radical or acetyl, $R^2$ denotes fluorine, chlorine or nitrile, m and n, independently of one another, represent one of the numbers 0, 1 or 2, X denotes fluorine or chlorine and Y represents a bridging member of the formula

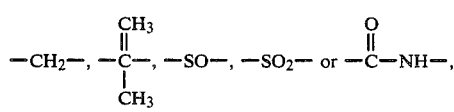

can be used as microbicidal agents. They can be prepared by reacting bisformanilides with a sulphenyl chloride in the presence of an acid-binding agent.

19 Claims, No Drawings

BIS[(FLUORO- AND CHLORO-METHYLTHIO)FORMAMIDES], A PROCESS FOR THEIR PREPARATION AND THEIR USE

The invention relates to new bis[(fluoro- and chloromethylthio)formamides], a process for their preparation and their use in microbicidal agents.

N-sulphenylated monoformanilides, which can be used as fungicides, are known from the German Offenlegungsschrift No. 2,838,750. However, because these known compounds have a high vapour pressure, their use is not unobjectionable.

New bis[(fluoro- and chloro-methylthio)formamides] of the formula

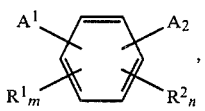 (I)

have been found in which
$A^1$ and $A^2$ are identical of different and represent the radical

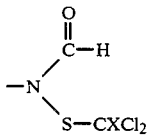

or the radical

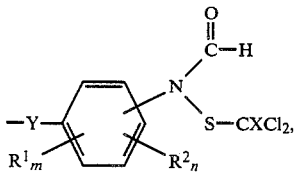

wherein
$R^1$ denotes an optionally halogenated lower alkyl or alkoxy radical or acetyl,
$R^2$ denotes fluorine, chlorine or nitrile,
m and n, independently of one another, represent one of the numbers 0, 1 or 2,
X denotes fluorine or chlorine and
Y represents a bridging member of the formula

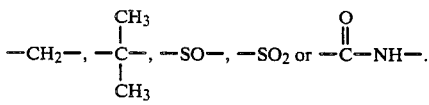

The new bis[(fluoro- and chloro-methylthio)formamides] have a low vapour pressure and may be used without problems, in particular in interior spaces. In addition, they have a greater microbicidal activity compared to the compounds known from the German Offenlegungsschrift No. 2,838,750.

According to the invention, lower alkyl radicals denote straight-chain or branched hydrocarbon radicals having 1 to, say, 6 carbon atoms. The following radicals may be mentioned as examples: methyl, ethyl, propyl, isopropyl, butyl, isobutyl, pentyl, isopentyl, hexyl and isohexyl. Preferred lower alkyl radicals are the methyl and the ethyl radical.

According to the invention, lower alkoxy radicals denote straight-chain or branched hydrocarbon radicals having 1 to, say, 6 carbon atoms and bonded via oxygen. The following radicals may be mentioned as examples: methoxy, ethoxy, propoxy, isopropoxy, butoxy, isobutoxy, pentoxy, isopentoxy, hexoxy and isohexoxy. Preferred lower alkoxy radicals are the methoxy and the ethoxy radical.

The lower alkyl and alkoxy radicals can be optionally substituted by halogen. Halogen denotes fluorine, chlorine, bromine and iodine, preferably fluorine and chlorine.

Preferred lower alkyl and alkoxy radicals substituted by halogen are the trifluoromethyl and trifluoromethyloxy radicals.

According to the invention, the bis[(fluoro- and chloro-methylthio)formamides] are preferred which have the formulae

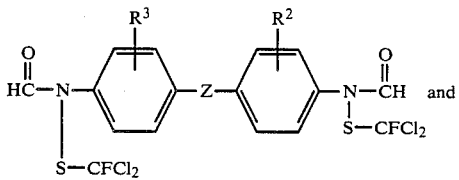 (II)

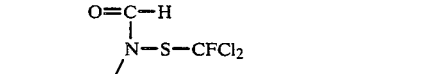

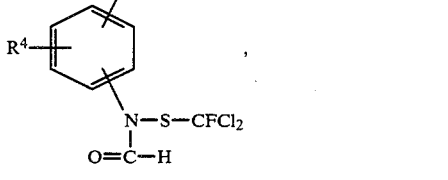 (III)

in which
Z represents the radicals

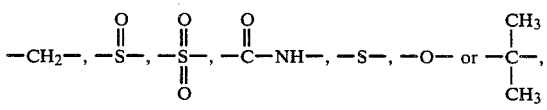

$R^3$ denotes hydrogen or chlorine and
$R^4$ denotes hydrogen, methyl, trifluoromethyl, nitro or chlorine.

The following new bis [(fluoro- and chloro-methylthio)formamides] may be mentioned as examples: bis(N-fluorodichloromethylsulphenyl-4-formamidophenyl)methane, bis(N-fluorodichloromethylsulphenyl-4-formamidophenyl)sulphone, bis(N-fluorodichloromethylsulphenyl-4-formamidophenyl)sulphoxide, bis(N-fluorodichloromethylsulphenyl-4-formamidophenyl)ether, bis(N-fluorodichloromethylsulphenyl-4-formamidophenyl)thioether, 1,4-bis(N-fluorodichloromethylsulphenylformamido)benzene, 1,2-bis(N-fluorodichloromethylsulphenylformamido)benzene, 1,3-bis(N-fluorodichloromethylsulphenylformamido)benzene, 1,3-bis(N-fluorodichloromethylsulphenylformamido)-4-methylbenzene, 1,3-bis(N-fluorodichloromethylsulphenylformamido)-4-trifluoromethylbenzene, 1,3-bis(N-fluorodichloromethylsulphenylformamido)-4- chlorobenzene, 1,3-bis(N-fluorodichloromethylsulphenylformamido)-4-nitrobenzene, 1,3-bis(fluorodichloromethylsulphenylformamido)-2,4-dichlorobenzene, 1,4-bis(N-fluorodichloromethylsulphenylformamido)-2-methylbenzene, 1,2-bis(N-fluorodichloromethylsulphenylformamido)-3,5-dimethylbenzene and 1,2-bis(N-fluorodichloromethylsulphenylformamido)-4-methylbenzene.

The new bis[(fluoro- and chloro-methylthio)formamides] can be prepared by reacting bisformanilides of the formula

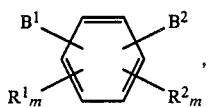
(IV)

in which $B^1$ and $B^2$ are identical or different and represent the radical

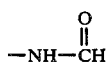

or the radical

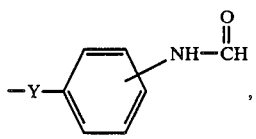

wherein $R^1$, $R^2$, m, n and Y have the abovementioned meaning, with a sulphenyl chloride of the formula

R—S—Cl     (V), in which R denotes fluorodichloromethyl or trichloromethyl, in the presence of an acid-binding agent and solvent in the temperature range from 0° to 40° C.

The bisformanilides used as starting compounds can be obtained by reaction of the aromatic diamines with formic acid (Houben-Weyl, Volume 8, page 654 [1952]) or, preferably, by reaction of the corresponding diisocyanates with anhydrous formic acid.

As acid-binding agents in the process according to the invention, acid-binding agents can be employed which, under the reaction conditions, bind the hydrogen chloride being liberated. Examples which may be mentioned are: alkali metal and alkaline earth metal hydroxides, such as sodium hydroxide, potassium hydroxide, magnesium hydroxide and calcium hydroxide, alkali metal and alkaline earth metal carbonates, such as sodium carbonate, potassium carbonate, magnesium carbonate and calcium carbonate, ammonia, amines, especially tertiary amines of the formula

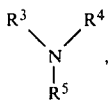
(VI)

in which $R^3$, $R^4$ and $R^5$ are identical or different and represent a lower straight-chain or branched alkyl radical (up to, say, 6 carbon atoms) or a phenyl radical.

Preferred bases are triethylamine and N,N-dimethylbenzylamine.

The process according to the invention can be carried out in the presence or absence of a solvent and/or diluene. Solvents and/or diluents which may be mentioned are inert organic solvents which are not changed under the reaction conditions. Examples which may be mentioned are toluene, dioxane, acetone, tert.-butanol or isopropanol. In addition, it is possible to carry out the process according to the invention in aqueous solution.

The starting products of the process according to the invention are generally employed in equivalent amounts. Obviously, it is possible to employ one or other of the reactants in excess, for example up to 2 mols.

The solvent and/or diluent is generally employed in an amount of 20 to 80% by weight, relative to the fluoro- and chloro-methylthioformamide.

The process according to the invention can, for example, be carried out as follows:

The bisformanilide is optionally diluted with a solvent and initially introduced into the reaction vessel. Subsequently, the sulphenic acid chloride and the acid-binding agent are added simultaneously and, after completion of the reaction, the mixture is washed with water. The organic phase containing the final product according to the invention is then separated off.

The bis[(fluoro- and chloro-methylthio)formamides] according to the invention can be used as active agents for the control of microorganisms, particularly in industrial materials. Industrial materials are inanimate materials, such as materials which have been manufactured for use in industry. Possible examples of industrial materials which are to be protected by the active agent according to the invention from microbial alteration and damage are adhesives, glues, papers and cardboards, textiles, leather, wood, e.g. lumber, coating agents, building materials, rubber and plastic articles, cooling lubricants and other materials which can be decomposed by microorganisms. Within the scope of the materials to be protected, there may be mentioned parts of production plants, for example cooling water circulations, which can be adversely affected by microorganisms. Industrial materials within the scope of the present invention which may preferably be mentioned are coating and impregnating agents for wood.

Examples of microorganisms which can bring about degradation or alteration of the industrial materials are bacteria, fungi, yeasts, algae and slimes. The bis[(fluoro- and chloro-methylthio)formamides] according to the invention preferentially act against fungi.

Examples of microorganisms which may be mentioned are those of the following genera: Coniophora, such as *Coniophora puteana,* Lentinus, such as *Lentinus tigrinus,* Pullularia, such as *Aureobasidium pullulans,* Sclerophoma, such as *Sclerophoma pityophila,* Aspergillus, such as *Aspergillus niger,* Alternaria, such as *Alternaria tenuis,* Chaetomium, such as *Chaetomium globosum,* Polyporus, such as *Polyporus versicolor,* Penicillium, such as *Penicillium glaucum* and Trichoderma, such as *Trichoderma viride.*

Depending on the area of application, the bis[(fluoro- and chloro-methylthio)formamides] according to the invention can be converted into the customary formulations, such as solutions, emulsions, suspensions, powders, pastes and granules. These can be prepared in a manner known in itself, for example, by mixing the active agents with a diluent, which consists of a liquid solvent and/or solid vehicles, if appropriate using surface-active agents, such as emulsifiers and/or dispersing agents, and in the case where, for example, aqueous extenders are used, organic solvents can be used as auxiliary solvents if necessary.

Examples of possible liquid solvents for the active agents are alcohols, for example lower aliphatic alcohols, preferably ethanol and isopropanol, and aromatic alcohols, such as benzyl alcohol, liquid hydrocarbons, such as petroleum fractions, chlorinated hydrocarbons, such as 1,2-dichloroethane, esters, such as diethylene glycol diacetate or ethyl acetate, ketones, such as cyclohexanone or acetone, dimethylformamide or dimethyl sulphoxide.

Examples of possible solid vehicles which are added in the preparation of the finished forms of the active agent for use are finely divided aluminium oxides, silicates, carbonates, iron oxide, gypsum or wood dust.

Possible surface-active agents are commercial emulsifiers, such as aryl and alkylsulphonates; ethoxylated alkylphenols, fatty acids, fatty alcohols or alkylamines or dispersing agents, such as polycarboxylic acids, polyvinyl alcohol, lignin, sulphite spent liquors or methylcellulose.

Forms for use of the microbicidal agents according to the invention generally contain 0.1 to 95% by weight, preferably 0.5 to 90% by weight, of the bis[(fluoro- and chloro-methylthio)formamides] according to the invention as active agent.

The amounts of active agent necessary for the protection of industrial materials can vary within wide ranges. In general, they are in the range from 0.001 to 5% by weight, preferably in the range from 0.01 to 2% by weight, relative to the total amount of the material to be protected.

The active agents according to the invention can be present in the formulations in mixtures with other known inorganic and organic fungicides, bactericides and/or insecticides. Examples of active agents which may be mentioned are the following: benzimidazolylmethyl carbamate, tetramethylthiuram disulphide, p-chloro-m-cresol, 1-[chlorophenyl-bis(phenyl)methyl-]imidazole, parathione and streptomycin.

EXAMPLE 1

Preparation (compound 1)

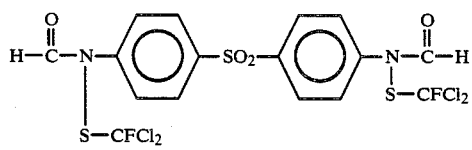

30.4 g of bis(4-formamidophenyl)sulphone (0.1 mol) are initially introduced into 150 ml of dry ethyl acetate and 33.8 g (0.2 mol) of dichlorofluoromethanesulphenyl chloride are added dropwise at 0° C. within 30 minutes. Subsequently, 20.2 g (0.2 mol) of triethylamine are added dropwise at 0° C. within 30 minutes. The mixture is maintained at 22° C. for 2 hours and then filtered. The solid material is suspended in ethanol, poured into ice-water and again filtered and dried.

Yield: 43 g
Melting point: 177° C.
Cl calculated: 24.8%; found: 24.0%.
The product is soluble in acetone and DMF.

EXAMPLE 2

Preparation (compound 2)

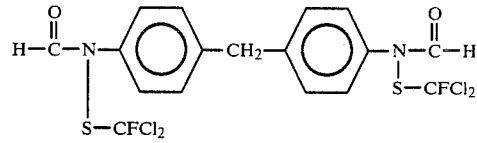

24.4 g (0.1 mol) of bis(4-formamidophenyl)methane are initially introduced into 150 ml of dry ethyl acetate and 33.8 g (0.2 mol) of dichlorofluoromethanesulphenyl chloride are added dropwise at 0° C. within 1 hour. Subsequently, 22.8 g (0.23 mol) of triethylamine are added dropwise at 0° C. within 20 minutes. The mixture is stirred at 20° C. for 1 hour. Thereafter it is worked up in analogy to Example 1.

Yield: 40 g
Melting point: 107° C.
Cl calculated: 27.3%; found: 26.9%.
The product is soluble in acetone, DMF and toluene.

EXAMPLE 3

Preparation (compound 3)

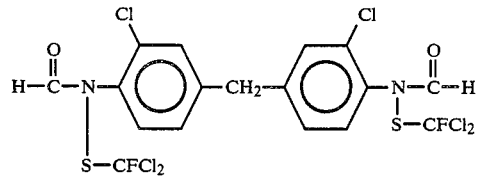

16.2 g (0.05 mol) of bis(3-chloro-4-formamidophenyl)methane are initially introduced into 100 ml of dry methylene chloride and 16.9 g (0.1 mol) of dichlorofluoromethanesulphenyl chloride are added dropwise at about 10° C. within 15 minutes. Subsequently, 10 g (0.1 mol) of triethylamine are added dropwise at about 16° C. within 45 minutes. The mixture is maintained at 40° C. for 1 hour, then treated with 3×50 ml of distilled water, filtered and the solvent is distilled off. The residue is dissolved in acetone and precipitated with water. The solid is filtered off and dried. A resinous product is obtained, which is, for example, soluble in acetone, ethyl acetate or toluene.

Yield: 20 g
Cl calculated: 35.5% found: 34.9%.

EXAMPLE 4

Preparation (compound 4)

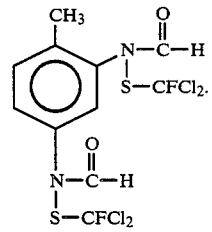

35.6 g (0.2 mol) of 2,5-diformamidotoluene are initially introduced into 100 ml of dry methylene chloride and 67.6 g (0.4 mol) of dichlorofluoromethanesulphenyl chloride are added dropwise at 20° C. within 45 minutes. Subsequently, 40 g (0.4 mol) of triethylamine are added dropwise at 20° C. within 1 hour 15 minutes. The temperature is maintained using a cooling bath. The mixture is then stirred at 20° C. for 1 hour, then filtered, extracted by shaking with 2×100 ml of distilled water, and the organic phase is separated off, dried with sodium sulphate and the methylene chloride is distilled off on a rotary evaporator. The residue remaining is 74.5 g of a resin which is soluble in acetone, methylene chloride, toluene, methanol, ethyl acetate and, to a slight extent, in white spirit.

Cl calculated: 31.9%; found: 31.6%.

EXAMPLE 5

Compounds according to the invention is graduated concentrations between 1 and 5,000 mg/l per trial sample were worked into an agar which was prepared from beer wort and peptone. After solidification of the agar, the agar samples thus prepared were contaminated with pure cultures of various test fungi (see table).

After storage for two weeks at 28° C. and 60 to 70% relative atmospheric humidity, evaluation was carried out. The minumum inhibitory concentration (MIC) is given in Table 2 as the lowest concentration of a substance in an agar sample at which no growth by the species used ensues.

| Test organisms | MIC values of bis[(fluoro- and chloro-methylthio)formamides] in mg/l according to Example No. | | |
|---|---|---|---|
| | 1 | 2 | 4 |
| Penicillium glaucum | 500 | 350 | 10 |
| Chaetomium globosum | 200 | 100 | 20 |
| Aspergillus niger | 750 | 350 | 20 |
| Alternaria tenuis | 20 | <10 | 5 |
| Aureobasidium pullulans | 200 | 35 | 10 |
| Sclerophoma pityophila | 200 | 35 | 15 |
| Lentinus tigrinus | <10 | <10 | 1.5 |
| Polyporus versicolor | 350 | 50 | 5 |
| Coniophora puteana | | <10 | 1.5 |

What is claimed is:

1. A bis[fluoro- or chloro-methylthio)formamide] of the formula

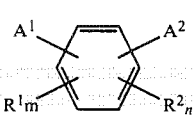

in which
A¹ and A² are identical or different and represent the radical

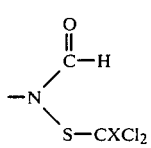

or the radical

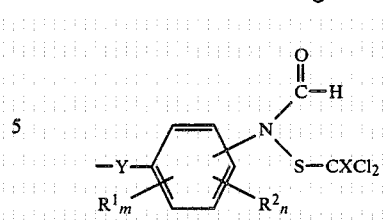

wherein
R¹ denotes an optionally halogenated lower alkyl or alkoxy radical or acetyl,
R² denotes fluorine, chlorine or nitrile,
m and m, independently of one another, represent one of the numbers 0, 1 or 2,
X denotes fluorine or chlorine and
Y represents a bridging member of the formula $$-CH_2-, -\underset{\underset{CH_3}{|}}{\overset{\overset{CH_3}{|}}{C}}-, -SO-, -SO_2- \text{ or } -\overset{\overset{O}{\|}}{C}-NH-.$$

2. A bis[(fluoro- or chloro-methylthio)formamides] according to claim 1, having the formula

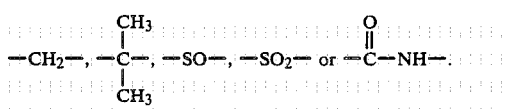

3. A bis[(fluoro- or chloro-methylthio)formamides] according to claim 1, having the formula

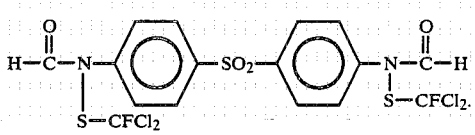

4. A bis[(fluoro- or chloro-methylthio)formamides] according to claim 1, having the formula

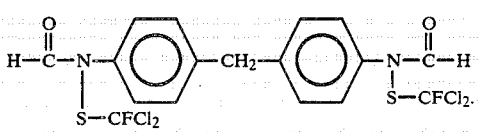

5. A bis[(fluoro- or chloro-methylthio)formamides] according to claim 1, having the formula

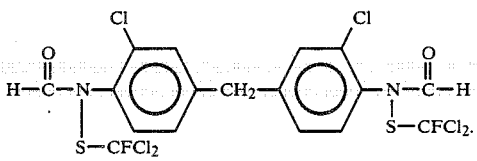

6. A bis[(fluoro- or chloro-methylthio)formamide] according to claim 1, wherein
A' represents the radical

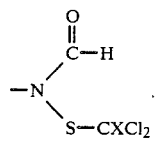

7. A bis[(fluoro- or chloro-methylthio)formamide] according to claim 1,
wherein
A' represents the radical

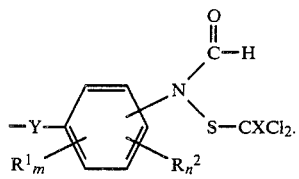

8. A bis[(fluoro- or chloro-methylthio)formamide] according to claim 1,
wherein
X denotes fluorine.

9. A bis[(fluoro- or chloro-methylthio)formamide] according to claim 1,
wherein
X denotes chlorine.

10. A bis[(fluoro- or chloro-methylthio)formamide] according to claim 1, wherein said bridging member is —CH$_2$—.

11. A bis[(fluoro- or chloro-methylthio)formamide] according to claim 1, wherein said bridging member is —C(CH$_3$)$_2$—.

12. A bis[(fluoro- or chloro-methylthio)formamide] according to claim 1, wherein said bridging member is —SO—.

13. A bis[(fluoro- or chloro-methylthio)formamide] according to claim 1, wherein said bridging member is —SO$_2$—.

14. A bis[(fluoro- or chloro-methylthio)formamide] according to claim 1, wherein said bridging member is —C(O)—NH—.

15. A process for preparing bis[(fluoro- or chloromethylthio)formamide] which comprises contacting a bis form anilide of the formula

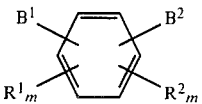

in which
B$^1$ and B$^2$ are identical or different and represent the radical

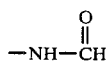

or the radical

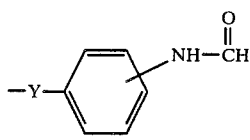

wherein
R$^1$, R$^2$, m, n and Y have the abovementioned meaning,
with a sulphenyl chloride of the formula

in which
R denotes fluorodichloromethyl or trichloromethyl, in the presence of an acid-binding agent and a solvent in the temperature range from 0° to 40° C.

16. A process according to claim 15, wherein said acid binding agent is triethylamine or N,N-dimethylbenzylamine.

17. A microbicidal composition according to claim 1, wherein said bis[(fluoro- or chloro-methylthio)formamide] is present in an amount of 0.1 to 95% by weight.

18. A process for protecting an industrial material against attack by a fungus, bacteria or insect which comprises applying thereto an effective amount of the bis[(fluoro- or chloro-methylthio)formamide] of claim 1.

19. A composition for control of bacteria, fungi, yeasts, algae and slimes comprising an effective amount of a [bis(fluoro- or chloro-methylthio)formamide] according to claim 1, and a diluent.

* * * * *

UNITED STATES PATENT AND TRADEMARK OFFICE
CERTIFICATE OF CORRECTION

PATENT NO. : 4,532,259
DATED : July 30, 1985
INVENTOR(S) : Helmut Ritter, et al.

It is certified that error appears in the above-identified patent and that said Letters Patent is hereby corrected as shown below:

| | |
|---|---|
| Col. 4, lines 7, 8 | Delete "diluene" and substitute --diluent-- |
| Col. 7, line 20 | Delete "is" and substitute --in-- |
| Col. 7, line 28 | Delete "minumum" and substitute --minimum-- |
| Col. 8, line 14 | Delete "m and m" and substitute --m and n-- |

Signed and Sealed this

Seventh Day of January 1986

[SEAL]

Attest:

Attesting Officer

DONALD J. QUIGG

Commissioner of Patents and Trademarks